United States Patent
Verdrel-Lahaxe et al.

(10) Patent No.: US 6,752,998 B2
(45) Date of Patent: Jun. 22, 2004

(54) EXOTHERMIC COSMETIC COMPOSITION

(75) Inventors: Delphine Verdrel-Lahaxe, Antony (FR); Lien Bui-Bertrand, Savigny sur Orge (FR)

(73) Assignee: L'Oreal, Paris (FR)

( * ) Notice: Subject to any disclaimer, the term of this patent is extended or adjusted under 35 U.S.C. 154(b) by 110 days.

(21) Appl. No.: 09/901,688

(22) Filed: Jul. 11, 2001

(65) Prior Publication Data

US 2002/0032135 A1 Mar. 14, 2002

(30) Foreign Application Priority Data

Jul. 11, 2000 (FR) .............................. 00 09062

(51) Int. Cl.$^7$ ............................ A61K 7/48; C11D 1/86; C11D 3/02

(52) U.S. Cl. .................. 424/401; 424/69; 510/131; 510/136; 510/137; 510/152; 510/155; 510/156; 510/157; 510/158; 510/404; 510/466; 510/486; 510/507; 510/511; 134/42

(58) Field of Search ................................ 510/131, 136, 510/137, 152, 155, 156, 157, 158, 404, 466, 486, 507, 511; 424/401, 69; 134/42

(56) References Cited

U.S. PATENT DOCUMENTS 4,626,550 A  12/1986  Hertzenberg .............. 514/770
6,153,208 A * 11/2000  McAtee et al. ............. 424/402
6,180,124 B1 * 1/2001  Ohta et al. .................. 424/401
2002/0032135 A1 * 3/2002  Verdrel-Lahaxe et al. .. 510/136
2002/0051798 A1  5/2002  Koike et al.

FOREIGN PATENT DOCUMENTS

| EP | 0 187 912 A2 | 7/1986 | |
| EP | 0 384 070 A2 | 8/1990 | |
| EP | 0 897 719 A1 | 2/1999 | |
| EP | 0 950 400 A2 | 10/1999 | |
| EP | 0 974 340 A2 | 1/2000 | |
| EP | 1172088 | * 1/2000 | ............ A61K/7/48 |
| EP | 1 051 964 A2 | 11/2000 | |
| EP | 1051964 | * 11/2000 | ............ A61K/7/48 |
| WO | WO 93/08793 | 5/1993 | |

* cited by examiner

Primary Examiner—Brian P. Mruk
(74) Attorney, Agent, or Firm—Oblon, Spivak, McClelland, Maier & Neustadt, P.C.

(57) ABSTRACT

One embodiment of the present invention provides an exothermic composition, which includes at least one zeolite; at least one surfactant; at least one magnesium or calcium halide; and a physiologically acceptable anhydrous medium. Another embodiment of the present invention provides a composition, which includes a means for making the composition exothermic; at least one surfactant; at least one magnesium or calcium halide; and a physiologically acceptable anhydrous medium. Other embodiments of the present invention provide processes for removing make-up from or cleansing the skin or mucous membrane, and articles which include the composition.

34 Claims, No Drawings

EXOTHERMIC COSMETIC COMPOSITION

BACKGROUND OF THE INVENTION

1. Field of the Invention

The present invention relates to exothermic compositions and to the uses of the composition for cleansing and/or for removing make-up from the skin and/or mucous membranes.

2. Discussion of the Background

It is known to use exothermic anhydrous cosmetic compositions, i.e., compositions which have a heating effect when applied to the skin. The exothermic nature of these compositions is generally provided by the presence of an exothermic compound such as zeolites and polyols, for example glycerol or polyethylene glycols. These compositions are particularly suitable for cleansing the skin. EP-A-974 340 discloses a polyol-based heating composition whose spreading and rinsing properties are improved by the presence of aluminium oxide.

Zeolites are particularly effective as exothermic compounds. However, in order for the exothermic compositions containing them to have good cleansing properties, it is necessary to add surfactants and in particular foaming surfactants thereto. EP-A-897 719 discloses a skin cleansing composition which includes a heat-generating compound, and in particular a zeolite, combined with an anionic surfactant. The addition of surfactants, particularly nonionic surfactants, to these compositions leads to instability of the composition, which is reflected by a heterogeneity of the composition. The zeolites have a tendency to migrate to the bottom, resulting in decantation in the composition. Such instability makes the composition unacceptable for use.

To improve the stability of the above-mentioned compositions, it has been considered to add thickening polymers such as carbopols. The addition of these polymers, however, has the drawback of resulting in sticky and runny gels, which, in addition, are not homogeneous.

Thus, there is still a need for a cleansing exothermic cosmetic composition, which is stable over time.

SUMMARY OF THE INVENTION

It is an object of the present invention to provide an exothermic composition.

It is another object of the present invention to provide an exothermic composition which is stable over time.

These and other objects are achieved by the present invention, which is defined in the claims. One embodiment of the present invention provides an exothermic composition, which includes:
  at least one zeolite;
  at least one surfactant;
  at least one magnesium or calcium halide; and
  a physiologically acceptable anhydrous medium.

Another embodiment of the present invention provides a composition, which includes:
  a means for making the composition exothermic;
  at least one surfactant;
  at least one magnesium or calcium halide; and
  a physiologically acceptable anhydrous medium.

Another embodiment of the present invention provides a process for removing make-up from or cleansing the skin or mucous membrane, which includes:
  moistening the skin or mucous membrane;
  applying an exothermic composition thereto;
  working the applied composition into a lather;
  rinsing the skin or mucous membrane; wherein
  the exothermic composition includes:
    at least one zeolite;
    at least one surfactant;
    at least one magnesium or calcium halide; and
    a physiologically acceptable anhydrous medium.

Another embodiment of the present invention provides a process for removing make-up from or cleansing the skin or mucous membrane, which includes:
  applying, to dry skin or mucous membrane, an exothermic composition;
  adding water to the applied composition;
  working the applied composition into a lather; and
  rinsing the skin or mucous membrane; wherein
  the exothermic composition includes:
    at least one zeolite;
    at least one surfactant;
    at least one magnesium or calcium halide; and
    a physiologically acceptable anhydrous medium.

Another embodiment of the present invention provides a method of stabilizing a composition, the composition including:
  at least one zeolite;
  at least one surfactant; and
  a physiologically acceptable anhydrous medium;
  the method including:
    contacting the composition with at least one magnesium or calcium halide.

Another embodiment of the present invention provides an article, which includes:
  a water-insoluble substrate; and
  an exothermic composition, which includes:
    at least one zeolite,
    at least one surfactant,
    at least one magnesium or calcium halide; and
    a physiologically acceptable anhydrous medium.

The present inventors have found, surprisingly, that the addition of a magnesium or calcium halide to an exothermic composition containing a zeolite and a surfactant gives a stable composition.

DESCRIPTION OF THE PREFERRED EMBODIMENTS

Various other objects, features and attendant advantages of the present invention will be more fully appreciated as the same becomes better understood from the following detailed description of the preferred embodiments of the invention.

The invention preferably relates to an exothermic cosmetic composition which includes, in a physiologically acceptable anhydrous medium, at least one zeolite, at least one surfactant and at least one a magnesium or calcium halide.

The expression "exothermic composition" means herein a composition such that the user experiences a heating sensation when the composition is applied to the skin. It is a composition whose temperature in the presence of water (water added during its use or the water present in the skin) may instantaneously rise by several degrees (one to twenty degrees). This heating effect allows better opening of the skin's pores and thus better cleansing of the skin.

The composition according to the invention includes an anhydrous medium. The term "anhydrous" means herein a medium which is virtually anhydrous, that is to say generally comprising less than 6% by weight of water, preferably less than 4% by weight of water and better still less than 1% by weight of water relative to the total weight of the composition. It may also be totally anhydrous. These ranges expressly include 5, 3, 2, 1.1, 0.9, 0.7, 0.5, 0.3, 0.1, and 0%.

Since the composition of the invention is preferably a cosmetic composition and preferably intended for topical application, it includes a physiologically acceptable medium, that is to say a medium which is compatible with the skin, mucous membranes and/or keratin fibres. A physiologically acceptable anhydrous medium herein comprises for example polyols such as glycerin, glycols such as butylene-glycol, and polyethylene-glycols.

Preferably, the composition of the invention is homogeneous and stable over time. It is generally in the form of a translucent to opaque gel, but it may also be in the form of a cream, a paste or even a powder if all the constituents used are powdery, the said powder possibly being used in powder form or in a sponge or alternatively impregnated on a wipe. The composition of the invention may be used, whatever its form, on a wipe.

The composition is stable and has a appropriate viscosity without even being necessary to add a gelling agent et especially a gelifying polymer. According to one preferred embodiment of the invention, the composition is free from water-soluble polymer.

The magnesium or calcium halide has the advantage not only of giving a stable composition but also of being able to adjust the pH of the composition to a value which is suitable for topical use, since the zeolites give the compositions containing them a high basic pH which is incompatible with topical use on the skin. The pH obtained for the composition according to the invention thus generally ranges from 5 to 9. This range expressly includes pH values of 6, 7 and 8.

The present invention relates also to the use of at least one magnesium or calcium halide in order to stabilize a composition comprising, in a physiologically acceptable anhydrous medium, at least one zeolite and at least one surfactant.

The magnesium or calcium halide may be chosen in particular from calcium and magnesium iodides, chlorides and bromides, and mixtures thereof. According to one preferred embodiment of the invention, the alkaline-earth metal halide is calcium chloride.

The amount of magnesium or calcium halide(s) may range, for example, from 1% to 15% by weight and preferably from 2% to 10% by weight relative to the total weight of the composition. These ranges expressly include 3, 4, 5, 6, 7, 8, 9, 11, 12, 13 and 14.

Zeolites are silicoaluminates. Zeolites which may be mentioned in particular include activated zeolites, and for example zeolites A, zeolites X such as those sold by the companies Fluka and Union Carbide, zeolites MAP such as those disclosed in EP-A-384 070 (the entire contents of which being hereby incorporated by reference), and activated zeolites A. The preferred cations present in the zeolites include Na, K, Ca, Zn, Mg, Li or Cu and combinations thereof. Activated zeolites which may be used in particular are the zeolites A-3, A-4 and A-5 of formula:

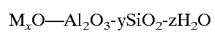

in which M is an alkali metal or alkaline-earth metal and x, y and z are, independently of each other, any number. These zeolites are in the form of particles preferably having a particle size ranging from 3 to 6 microns. Mixtures of zeolites are possible.

Preferably, the alkali metal or alkaline earth metal used for M in the above formula may be chosen from Na, K, Mg, and Ca.

Preferably, the x, y and z in the above formula each independently range from 1–75, more preferably 1–50, more particularly preferably 2–25, and most preferably 3–15. These ranges expressly include 4, 5, 6, 7, 8, 9 and 20.

These zeolites and the process for preparing them are disclosed in EP-A-187 912, U.S. Pat. No. 4,626,550, incorporated herein in its entirety by reference. It is especially preferable to use those sold under the name Advera 401N and Advera 402N by the company PQ Corporation.

Any other exothermic agent, and thus an agent capable of releasing heat during hydration of the composition, and in particular one or more polyols, may be added to the zeolite or to the zeolites used in the composition of the invention.

Polyols which may be mentioned in particular include polyols containing at least 2 hydroxyl groups and at least 3 carbon atoms, and, for example, glycerol, diglycerol, propylene glycol, dipropylene glycol, butylene glycol, hexylene glycol, polyethylene glycol and polyethylene glycols with a molecular weight of less than 600, for instance PEG-8, and sugars such as sorbitol, and mixtures thereof. The polyols preferably used are glycerol, butylene glycol, propylene glycol, dipropylene glycol and PEG-8, and mixtures thereof.

According to one preferred embodiment of the invention, the composition contains a zeolite or a mixture of zeolites, and preferably a mixture of zeolite(s) and of polyol(s) and more particularly a mixture of activated zeolite and of one or more polyols chosen from butylene glycol, propylene glycol, glycerol, dipropylene glycol and/or PEG-8.

The amount of exothermic agent (zeolite(s) or of zeolite (s) with added polyols) should be sufficient for the composition to be exothermic and, consequently, for the user to effectively experience a heating sensation when the composition is applied to the skin. In practice, the amount of zeolite(s) generally ranges from 5% to 95% by weight, preferably from 10% to 70% by weight and better still from 20% to 60% by weight relative to the total weight of the composition. The amount of polyol(s) may range, for example, from 20% to 90%, preferably from 30% to 90% by weight and better still from 40% to 90% by weight relative to the total weight of the composition. The ranges for the amount of zeolite(s) expressly include 6, 7, 9, 11, 15, 19, 21, 30, 40, 50, 55, 65, 75 and 90%. The ranges for the amount of polyol(s) expressly include 21, 25, 29, 31, 35, 45, 55, 75, 85, 88 and 89%.

The composition according to the invention contains at least one surfactant which is preferably a cleansing and/or foaming surfactant, and which may be chosen from nonionic surfactants, anionic surfactants and amphoteric surfactants, and mixtures thereof. The amount of surfactant(s) may range from 0.5% to 20% by weight of active material, preferably from 1% to 15% by weight and better still from 2% to 10% by weight of active material relative to the total weight of the composition. These ranges expressly include 0.75, 3, 4, 5, 8, 9, 12, 14, 16, 18 and 19%. The surfactants may be in the form of powder, paste or liquid. They may also be in aqueous dispersion provided that the amount of water is not too large and does not impair the exothermic qualities of the composition.

The surfactant(s) is(are) advantageously in the form of a paste.

Preferable nonionic surfactants which may be used in the invention include, for example, of condensates of alkylene oxides and of alkylphenols such as ethoxylated octylphenol, such as the product sold under the name Triton X45 by the company Rohm & Haas; alkylpolyglucosides; ethers of fatty alcohols and of polyols such as, for example, Polyglyceryl-3 hydroxylauryl ether (CTFA name) sold under the name Chimexane NF by the company Chimex; nonionic derivatives of glucose and of methylglucose, comprising polyethylene oxide or polypropylene oxide groups, these derivatives optionally comprising a C8 to C30 fatty chain, such as oxyethylenated (120 EO) methylglucose dioleate (CTFA name: PEG-120 methylglucose dioleate) sold under the name Glucamate DOE 120 by the company Amerchol or oxypropylated (20 PO) methylglucose sold under the trade name Glucam E 20 by the company Amerchol; oxyethylenated fatty amides such as PEG-5 cocamide, and mixtures of these surfactants.

Preferable anionic surfactants which may be mentioned, for example, include polyalkylene glycol ethers of fatty alcohols; taurates; acyl lactylates such as sodium stearoyl lactylate (for example Pationic SSL sold by the company Maprecos); alkyl sulphates such as sodium lauryl sulphate (Sipon LCS sold by the company Henkel); glyceryl alkyl sulphates such as sodium cocoglyceryl sulphate (sold by the company Nikko under the name Nikkol SGC-80N); polyoxyethylenated alkyl sulphates; alkyl ether sulphates such as monoethanolamine lauryl ether sulphate; alkyl ether carboxylates; monoalkyl or dialkyl phosphates such as arginine monohexyl-2-decyl phosphate (MAP-16G-ARG sold by the company Kao Chemicals); ethoxylated alkyl phosphates; N-acylsarcosinates such as sodium myristoylsarcosinate (for example Nikkol Sarcosinate MN sold by the company Nikko); N-acylglutamates such as sodium lauroylglutamate (for example Amisoft LS11 sold by the company Ajinomoto); acylisethionates such as sodium cocoyl-isethionate sold in particular by the company Jordan (Jordapon CI); succinamates; soaps such as potassium or sodium laurate, myristate, palmitate or stearate; and mixtures thereof.

Preferable amphoteric or zwitterionic surfactants which may be mentioned, for example, include betaines and betaine derivatives; sultaines and sultaine derivatives; imidazolinium derivatives such as disodium cocoamphodiac-etate; and mixtures thereof.

According to one preferred embodiment of the invention, the surfactant is a nonionic surfactant, a mixture of nonionic surfactants or a mixture of nonionic and anionic surfactants.

The composition may also contain one or more other ingredients, in particular lipophilic ingredients, conventionally used in cleansing or make-up-removing compositions. These ingredients are, in particular, oils, fragrances, preserving agents, antioxidants, sequestering agents, fillers, colorants, cosmetic or dermatological active agents, or mixtures thereof. These adjuvants are used in the usual proportions for cleansing and/or care compositions, and, for example, from 0.01% to 10% relative to the total weight of the composition. Mixtures are possible. These adjuvants must be of a nature and must be used in an amount such that they do not disrupt the properties desired for the composition of the invention.

Preferable fillers which may be mentioned, for example, include talc, modified or unmodified starch, and in particular starches esterified with octenylsuccinic anhydride and more particularly "aluminium starch octenylsuccinate" such as the product sold by the company National Starch under the name Dry-Flo. Mixtures are possible.

Preferable active agents which may be used in the invention include, for example, antibacterial agents such as octopirox and triclosan, keratolytic agents such as salicylic acid, essential oils and vitamins, and in particular niacinamide (vitamin PP) and panthenol (vitamin B5).

The composition of the invention is particularly suitable for cleansing and/or removing make-up from the skin and/or mucous membranes and more particularly for cleansing and/or removing make-up from the skin.

A subject of the invention is also the cosmetic use of the composition as defined above, for cleansing and/or removing make-up from the skin and/or mucous membranes.

The composition of the invention is preferably in the form of a thick gel. Preferably, this gel maybe used in 2 ways:

(1) the face is moistened slightly and the gel is then applied to the face: the exothermic reaction then takes place. The gel is then worked into a lather by adding water, after which it is rinsed off; or (2) the gel is applied to dry skin by massaging; the exothermic reaction then starts by virtue of the hydration water of the skin, after which a small amount of water is added to increase the exothermic reaction, the gel is worked into a lather and is then rinsed off.

Thus, a further subject of the invention is a cosmetic process for removing make-up from and/or for cleansing the skin, which comprises or consists of slightly moistening the skin, and in particular the facial skin, in applying the composition as defined above to the skin, in working the composition into a lather by adding water, and finally in rinsing the skin.

A subject of the invention is also a cosmetic process for removing make-up from and/or for cleansing the skin, which comprises or consists of applying the composition as defined above to dry skin by massaging, in adding a small amount of water, in working the composition into a lather and then in rinsing the skin. As above-mentioned, the composition of the invention may be used on a substrate such as a sponge or a wipe, and preferably constitutes a disposable cleansing article.

Thus, the present invention relates also to a cleansing article which includes a water-insoluble substrate and a composition such as above-defined. The water-insoluble substrate may be a sponge or a wipe, for example a wipe from nonwoven material, with one or several (two or more) layers, the wipe being dry or humid.

EXAMPLES

Having generally described this invention, a further understanding can be obtained by reference to certain specific examples which are provided herein for purposes of illustration only and are not intended to be limiting unless otherwise specified. The amounts therein are given as % by weight.

Example 1

Heating Cleansing Composition

| | |
|---|---|
| Butylene glycol | 18% |
| PEG-8 | 18% |
| Glycerol | 14% |
| Polyglyceryl-3 hydroxylauryl ether | 6% |
| PEG-120 methyl glucose dioleate | 1% |
| Zeolite (activated potassium aluminosilicate: Advera 402 N) | 40% |
| Calcium chloride | 3% |

Procedure

The calcium chloride is dissolved in the PEG-8 and the butylene glycol. The molten surfactants are then added to the glycerol at 65° C. These 2 phases are homogenized, the mixture is cooled to room temperature and the zeolite is then added while homogenizing.

The product obtained is a stable white gel, which is easy to apply and to remove, and which has a soft feel and good cleansing power.

Comparative Example 1

Example 1 was repeated but without calcium chloride. Instability of the composition was observed, with decantation of the zeolite to the bottom and decantation of the glycols to the top.

Example 2

Heating Cleansing Composition

| | |
|---|---|
| Butylene glycol | 25% |
| PEG-8 | 25% |
| Glycerol | 12% |
| PEG-5 cocamide | 6% |
| PEG-120 methyl glucose dioleate | 2% |
| Zeolite (activated potassium aluminosilicate: Advera 402 N) | 20% |
| Calcium chloride | 10% |

The procedure is identical to that of Example 1.

The product obtained is a stable white gel, which is easy to apply and to remove, and which has a soft feel and good cleansing power.

Examples 3 and 4 and Comparative Examples 2 and 3

| Composition | Example 3 of the invention | Example 4 of the invention | Comparative Example 2 | Comparative Example 3 |
|---|---|---|---|---|
| PEG-8 | 14.3 | 14.3 | 14.3 | 14.3 |
| Butylene glycol | 14.3 | 14.3 | 14.3 | 14.3 |
| CaCl2, 2 H2O | 3 | 0 | 0 | 0 |
| NaCl | 0 | 0 | 3 | 0 |
| MgCl2, 6 H2O | 0 | 3 | 0 | 0 |
| Dimethicone copolyol | 2 | 2 | 2 | 2 |
| Glycerol | 27 | 24 | 24 | 24 |
| PEG-120 methyl glucose dioleate | 1 | 1 | 1 | 1 |
| Zeolite | 30 | 30 | 30 | 30 |
| Fillers: Kaolin + titan oxide + nacres | 11.4 | 11.4 | 11.4 | 11.4 |
| Viscosity (Poises) | 255 | 170 | Not determined because NaCl remains insoluble. | 88 |

The comparative Example 3 without salt has a viscosity which is clearly smaller than those of the examples according to the invention. This table shows that calcium and magnesium salts allow to stabilize the composition and to obtain an appropriate viscosity without using gelifying polymer.

Furthermore, in the examples of the invention, magnesium or calcium salt is dissolved in polyols. On the other hand, in comparative example 2, the salt (sodium chloride) remains insoluble and the desired aim is not obtained. Thus, the use of NaCl does not result in a stabilized composition.

Obviously, numerous modifications and variations of the present invention are possible in light of the above teachings. It is therefore to be understood that within the scope of the appended claims, the invention may be practiced otherwise than as specifically described herein.

This application is based on French patent application FR 0009062, filed Jul. 11, 2000, the entire contents of which are hereby incorporated by reference, the same as if set forth at length.

What is claimed is:

1. An exothermic composition, comprising:
   at least one zeolite;
   at least one surfactant;
   at least one magnesium or calcium halide; and
   a physiologically acceptable anhydrous medium.

2. The composition according to claim 1, wherein the magnesium or calcium halide is selected from the group consisting of calcium iodide, magnesium iodide, calcium chloride, magnesium chloride, calcium bromide, magnesium bromide, and mixtures thereof.

3. The composition according to claim 1, comprising calcium chloride.

4. The composition according to claim 1, wherein the halide is present in an amount ranging from 1% to 15% by weight relative to the total weight of the composition.

5. The composition according to claim 1, wherein the zeolite is an activated zeolite selected from the group consisting of zeolite A, zeolite X, zeolite MAP, and mixtures thereof.

6. The composition according to claim 1, wherein the zeolite is present in an amount ranging from 5% to 95% by weight relative to the total weight of the composition.

7. The composition according to claim 1, further comprising at least one polyol.

8. The composition according to claim 1, further comprising at least one polyol selected from the group consisting of glycerol, diglycerol, propylene glycol, dipropylene glycol, butylene glycol, hexylene glycol, polyethylene glycols, sugars, and mixtures thereof.

9. The composition according to claim 1, further comprising at least one polyethylene glycol having a molecular weight of less than 600.

10. The composition according to claim 1, further comprising at least one polyol in an amount ranging from 20% to 90% by weight relative to the total weight of the composition.

11. The composition according to claim 1, further comprising at least one polyol.

12. The composition according to claim 1, wherein the surfactant is selected from the group consisting of cleansing surfactant, foaming surfactant, and combinations thereof.

13. The composition according to claim 1, wherein the surfactant is selected from the group consisting of nonionic surfactant, anionic surfactant, amphoteric surfactant, and mixtures thereof.

14. The composition according to claim 1, wherein the surfactant is one or more nonionic surfactants selected from the group consisting of condensate of alkylene oxide and of alkylphenol; alkylpolyglucoside; ether of fatty alcohol and of polyol; nonionic derivative of glucose and of methylglucose, comprising one or more polyethylene oxide or polypropylene oxide groups and optionally comprising one or more C8 to C30 fatty chain; oxyethylenated fatty amide; and mixtures thereof.

15. The composition according to claim 1, wherein the surfactant is one or more surfactants selected from the group consisting of polyalkylene glycol ether of fatty alcohol, taurate, acyl lactylate, alkyl sulphate, glyceryl alkyl sulphate, polyoxyethylenated alkyl sulphate, alkyl ether sulphate, alkyl ether carboxylate, monoalkyl or dialkyl phosphate, ethoxylated alkyl phosphate, N-acylsarcosinate, N-acylglutamate, acylisethionate, succinamate, soap, and mixtures thereof.

16. The composition according to claim 1, wherein the surfactant is present in an amount ranging from 0.5% to 20% by weight relative to the total weight of the composition.

17. The composition according to claim 1, which is in at least one form selected from the group consisting of a gel, a cream, a paste, and a powder.

18. A composition, comprising:
   a means for making said composition exothermic;
   at least one surfactant;
   at least one magnesium or calcium halide; and
   a physiologically acceptable anhydrous medium.

19. A process for removing make-up from or cleansing the skin or mucous membrane, comprising:
   moistening the skin or mucous membrane;
   applying an exothermic composition thereto;
   working the applied composition into a lather;
   rinsing the skin or mucous membrane; wherein
   the exothermic composition comprises:
      at least one zeolite;
      at least one surfactant;
      at least one magnesium or calcium halide; and
      a physiologically acceptable anhydrous medium.

20. The process according to claim 19, wherein working the composition into a lather further comprises adding water to the applied composition.

21. A process for removing make-up from or cleansing the skin or mucous membrane, comprising:
   applying, to dry skin or mucous membrane, an exothermic composition;
   adding water to the applied composition;
   working the composition into a lather; and
   rinsing the skin or mucous membrane; wherein
   the exothermic composition comprises:
      at least one zeolite;
      at least one surfactant;
      at least one magnesium or calcium halide; and
      a physiologically acceptable anhydrous medium.

22. The process according to claim 21, wherein applying the composition to dry skin or mucous membrane comprises massaging.

23. A method of stabilizing a composition, the composition comprising:
   at least one zeolite;
   at least one surfactant; and
   a physiologically acceptable anhydrous medium;
   the method comprising:
      contacting said composition with at least one magnesium or calcium halide.

24. An article, comprising:
   a water-insoluble substrate; and
   an exothermic composition, comprising:
      at least one zeolite,
      at least one surfactant,
      at least one magnesium or calcium halide; and
      a physiologically acceptable anhydrous medium.

25. The composition according to claim 1, wherein said composition is free from water soluble polymer.

26. The composition according to claim 2, wherein said composition is free from water soluble polymer.

27. The composition according to claim 5, wherein said composition is free from water soluble polymer.

28. The composition according to claim 8, wherein said composition is free from water soluble polymer.

29. The composition according to claim 1, wherein the magnesium or calcium halide is selected from the group consisting of calcium iodide, magnesium iodide, calcium chloride, magnesium chloride, calcium bromide, magnesium bromide, and mixtures thereof,
   wherein the halide is present in an amount ranging from 1% to 15% by weight relative to the total weight of the composition,
   wherein the zeolite is an activated zeolite selected from the group consisting of zeolite A, zeolite X, zeolite MAP, and mixtures thereof,
   wherein the zeolite is present in an amount ranging from 5% to 95% by weight relative to the total weight of the composition,
   wherein the surfactant is one or more surfactants selected from the group consisting of condensate of alkylene oxide and of alkylphenol; alkylpolyglucoside; ether of fatty alcohol and of polyol; nonionic derivative of glucose and of methylglucose, comprising one or more polyethylene oxide or polypropylene oxide groups and optionally comprising one or more C8 to C30 fatty chain; oxyethylenated fatty amide; polyalkylene glycol ether of fatty alcohol, taurate, acyl lactylate, alkyl sulphate, glyceryl alkyl sulphate, polyoxyethylenated alkyl sulphate, alkyl ether sulphate, alkyl ether carboxylate, monoalkyl or dialkyl phosphate, ethoxylated alkyl phosphate, N-acylsarcosinate, N-acylglutamate, acylisethionate, succinamate, soap, and mixtures thereof,
   wherein the surfactant is present in an amount ranging from 0.5% to 20% by weight relative to the total weight of the composition.

30. The composition according to claim 29, wherein said composition is free from water soluble polymer.

31. The process according to claim 19, wherein said composition is free from water soluble polymer.

32. The process according to 21, wherein said composition is free from water soluble polymer.

33. The method according to claim 23, wherein said composition is free from water soluble polymer.

34. The article according to claim 24, wherein said composition is free from water soluble polymer.

* * * * *